(12) United States Patent
Gauzner et al.

(10) Patent No.: US 9,797,924 B2
(45) Date of Patent: Oct. 24, 2017

(54) CALIBRATION STANDARD WITH PRE-DETERMINED FEATURES

(71) Applicant: SEAGATE TECHNOLOGY LLC, Cupertino, CA (US)

(72) Inventors: Gennady Gauzner, San Jose, CA (US); Zhaoning Yu, Palo Alto, CA (US); Nobuo Kurataka, Campbell, CA (US); David S. Kuo, Palo Alto, CA (US); Kim Y Lee, Fremont, CA (US); Yautzong Hsu, Fremont, CA (US); Hong Ying Wang, Fremont, CA (US)

(73) Assignee: Seagate Technology LLC, Cupertino, CA (US)

( * ) Notice: Subject to any disclaimer, the term of this patent is extended or adjusted under 35 U.S.C. 154(b) by 91 days.

(21) Appl. No.: 14/783,403

(22) PCT Filed: Apr. 17, 2013

(86) PCT No.: PCT/US2013/036876
§ 371 (c)(1),
(2) Date: Oct. 8, 2015

(87) PCT Pub. No.: WO2014/171929
PCT Pub. Date: Oct. 23, 2014

(65) Prior Publication Data
US 2016/0069929 A1    Mar. 10, 2016

(51) Int. Cl.
*B32B 3/02*    (2006.01)
*G01Q 40/02*    (2010.01)
(Continued)

(52) U.S. Cl.
CPC .............. *G01Q 40/02* (2013.01); *G01N 21/01* (2013.01); *G01Q 40/00* (2013.01); *G03F 7/0002* (2013.01);
(Continued)

(58) Field of Classification Search
CPC ........ G01C 40/00; G01C 40/02; G01N 21/01; G01N 2201/13; H01J 37/261; H01J 37/263; G03F 7/0002
See application file for complete search history.

(56) References Cited

U.S. PATENT DOCUMENTS

2013/0143002 A1* 6/2013 Kurataka ............... G11B 5/855
428/172

* cited by examiner

*Primary Examiner* — Elizabeth Mulvaney (57) ABSTRACT

Provided herein in an apparatus, including a substrate; a functional layer, wherein the functional layer has a composition characteristic of a workpiece of an analytical apparatus; and pre-determined features configured to calibrate the analytical apparatus. Also provided herein is an apparatus, including a functional layer overlying a substrate; and pre-determined features for calibration of an analytical apparatus configured to measure the surface of a workpiece, wherein the functional layer has a composition similar to the workpiece. Also provided herein is a method, including providing a lithographic calibration standard having a functional layer to an analytical apparatus, wherein the functional layer has a composition characteristic of a workpiece of the analytical apparatus; providing calibration standard specifications to a computer interfaced with the analytical apparatus; and calibrating the analytical apparatus in accordance with calibration standard readings and the calibration standard specifications.

20 Claims, 4 Drawing Sheets

(51) Int. Cl.
*G01Q 40/00* (2010.01)
*G03F 7/00* (2006.01)
*H01J 37/26* (2006.01)
*G01N 21/01* (2006.01)

(52) U.S. Cl.
CPC .......... *H01J 37/261* (2013.01); *H01J 37/263* (2013.01); *G01N 2201/13* (2013.01); *H01J 2237/2602* (2013.01); *H01J 2237/2826* (2013.01)

CALIBRATION STANDARD WITH PRE-DETERMINED FEATURES

BACKGROUND

Instrumental analysis may be performed on an article of manufacture for the purpose of quality control before the article of manufacture is provided to an external market. To provide meaningful results for quality control, an analytical instrument is calibrated beforehand. An operator of the analytical instrument is often responsible for calibrating the analytical instrument, which often involves a subjective determination based on manually reading a calibration standard with the analytical instrument being calibrated. Calibrating the analytical instrument may be somewhat arbitrary as a result of the subjective determination, as well as time consuming as a result of the manual reading process. Moreover, variability in calibration quality between operators may compromise the establishment of quality trend data for manufacturing process improvement.

SUMMARY

Provided herein in an apparatus, including a substrate; a functional layer, wherein the functional layer has a composition characteristic of a workpiece of an analytical apparatus; and pre-determined features configured to calibrate the analytical apparatus. Also provided herein is an apparatus, including a functional layer overlying a substrate; and pre-determined features for calibration of an analytical apparatus configured to measure the surface of a workpiece, wherein the functional layer has a composition similar to the workpiece. Also provided herein is a method, including providing a lithographic calibration standard having a functional layer to an analytical apparatus, wherein the functional layer has a composition characteristic of a workpiece of the analytical apparatus; providing calibration standard specifications to a computer interfaced with the analytical apparatus; and calibrating the analytical apparatus in accordance with calibration standard readings and the calibration standard specifications. These and other features, aspects, and advantages of the invention may be better understood with reference to the following drawings, description, and appended claims.

DESCRIPTION

Before the invention is described in greater detail, it should be understood by persons having ordinary skill in the art to which the invention pertains that the invention is not limited to the particular embodiments described and/or illustrated herein, as elements in such embodiments may vary. It should likewise be understood that a particular embodiment described and/or illustrated herein has elements which may be readily separated from the particular embodiment and optionally combined with any of several other embodiments or substituted for elements in any of several other embodiments described herein.

It should also be understood by persons having ordinary skill in the art to which the invention pertains that the terminology used herein is for the purpose of describing the invention and particular embodiments thereof, and the terminology is not intended to be limiting. Unless indicated otherwise, ordinal numbers (e.g., first, second, third, etc.) are used to distinguish or identify different elements or steps in a group of elements or steps, and do not supply a serial or numerical limitation on the elements or steps of the claimed invention, or embodiments thereof. For example, "first," "second," and "third" elements or steps need not necessarily appear in that order, and the invention, or embodiments thereof, need not necessarily be limited to three elements or steps. It should also be understood that, unless indicated otherwise, any labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. It should also be understood that the singular forms of "a," "an," and "the" include plural references unless the context clearly dictates otherwise.

Unless defined otherwise, all technical and scientific terms used herein have the same meaning as commonly understood by persons of ordinary skill in the art to which the invention pertains.

The invention will now be described in greater detail.

An operator of the analytical instrument is often responsible for calibrating the analytical instrument, which often involves a subjective determination based on manually reading a calibration standard with the analytical instrument being calibrated. Calibrating the analytical instrument may be somewhat arbitrary as a result of the subjective determination, not to mention time consuming as a result of the manual reading process. Moreover, variability in calibration quality between operators may compromise the establishment of quality trend data for manufacturing process improvement.

Provided herein are calibration methods and calibration standards that may automate calibration of analytical instruments and may remove or reduce subjective determinations made by analytical instrument operators. Analytical apparatus that may be calibrated with calibration methods and calibration standards provided herein include, but are not limited to, optical surface analyzers, magnetic read-write head space analyzers, scanning probe microscopes (e.g., atomic force microscopy ["AFM"], scanning tunneling microscopy ["STM"], etc.), electron microscopes (e.g., transmission electron microscope ["TEM"], scanning electron microscope ["SEM"], reflection electron microscope ["REM"], scanning transmission electron microscope ["STEM"], low-voltage electron microscope ["LVEM"], etc.), an X-ray scatterometer (e.g., analytical instruments for small-angle X-ray scattering ["SAXS"]; wide-angle X-ray scattering ["WAXS"]; Compton scattering; X-ray Raman scattering, etc.), or an X-ray diffractometer.

Figure 1:
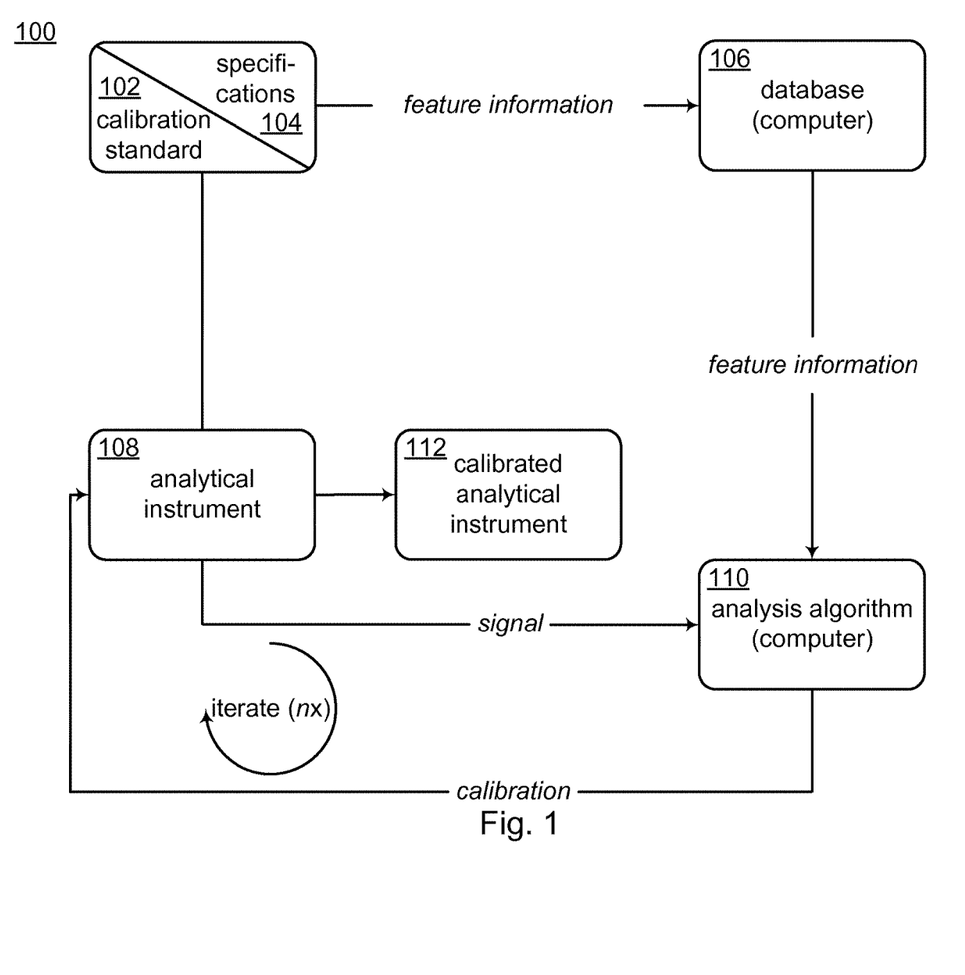
FIG. 1 provides a method by which an analytical instrument may be calibrated in an embodiment.

Turning to FIG. 1, FIG. 1 provides an embodiment of a method by which an analytical instrument may be calibrated. Calibration method 100 commences with calibration standard 102 and specifications 104, which specifications 104 are in accordance with the calibration standard 102 and pre-determined features of the calibration standard 102. Prior to calibration, feature information (i.e., information with respect to pre-determined features of the calibration standard 102, and information that may be used to discriminate among random contamination) from the specifications 104 may be provided to a database 106 on a computer. The calibration standard 102 may be provided to the analytical instrument 108, which analytical instrument 108 may be interfaced with the same computer or a different computer than that holding the database 106. During calibration, the analytical instrument 108 may read one or more pre-determined features of the calibration standard 102, produce a signal with respect to the one or more pre-determined features of the calibration standard 102, and provide the signal to software for operating the analytical instrument 108 or a software module thereof. Feature information located in database 106 (or on a storage medium for digitized information as described herein below) may be fetched by the software (or the software module) for operating the analytical instrument 108. An algorithm 110 of the software (or the software module) for operating the analytical instrument 108 may subsequently process the signal from the analytical instrument 108, determine the differences between the signal and the feature information from the database 106, and calibrate the analytical instrument 108 to minimize differences between the signals from calibration standard 102 readings and feature information from specifications 104. Such a calibration may be iteratively performed, optionally with additional calibration standards, until the analytical instrument 108 is appropriately calibrated for use (e.g., meets guidelines of a quality management system). Additional details are described in further detail below.

Calibration standards such as calibration standard 102 of FIG. 1 may be lithographic calibration standards prepared with pre-determined features in accordance with a lithographic process as provided herein below. Calibration standards may be disks, intermediates for which are provided in FIG. 3A and FIG. 3B; however, calibration standards are not limited to disks, as any form suitable for calibration of an analytical instrument may be prepared in accordance with a lithographic process as provided herein below.

Calibration standards may comprise a substrate; at least one functional layer; at least one feature layer; and, optionally, one or more finish layers. The substrate and any subsequent layers of a calibration standard may mimic a workpiece of an analytical instrument in structure and/or composition at a particular stage of manufacture, wherein the particular stage of manufacture is the stage of manufacture for which a workpiece is to be analyzed, for example, for quality control, after calibration of the analytical instrument. A calibration standard, for example, may mimic a workpiece, or a portion thereof, from a first stage of manufacture through a particular stage of manufacture. A calibration standard, for example, may mimic a workpiece, or a portion thereof, from an $n^{th}$ stage (e.g., a second stage, third stage, fourth stage, etc.) of manufacture up to a particular stage of manufacture. It may be more cost effective for a calibration standard to mimic a workpiece from an $n^{th}$ stage of manufacture up to a particular stage of manufacture when earlier manufacturing stages (e.g., <$n^{th}$ stage, such as $(n-1)^{th}$ stage, $(n-2)^{th}$ stage, $(n-3)^{th}$ stage, etc.) have little or no effect on the analysis.

With respect to the substrate, the substrate may comprise any material suitable for the lithographic process provided herein below. For example, the substrate may comprise any material suitable for sputtering, electroplating, atomic layer deposition ("ALD"), chemical vapor deposition "CVD"), evaporation, ion beam deposition ("IBD"), or the like, as such techniques may be used to provide the at least one functional layer; the at least one feature layer; and, optionally, the one or more finish layers. As such, the substrate may comprise, but is not limited to, a material such as silicon, quartz, glass, or aluminum. Examples of the foregoing include, but are not limited to, silicon wafers, quartz wafers, glass disks, and aluminum disks. See FIG. 2 and FIG. 4 for an example of a calibration standard 102 comprising a substrate 220.

With respect to the functional layer, the functional layer may comprise a single layer or a plurality of layers depending upon the analytical apparatus and/or the workpiece (e.g., a workpiece of a product at a particular stage of manufacture) for which the calibration standard is designed. The functional layer of a calibration standard includes, but is not limited to, a single layer or a plurality of layers corresponding to the single layer or the plurality of layers responsible for a workpiece's function up to a particular stage of manufacture. The functional layer may comprise any material suitable for the lithographic process provided herein below, including, but not limited to, a metal, an oxide (e.g., a metal oxide), silicon, silicon dioxide, a polymer, carbon, etc. For example, a calibration standard corresponding to a perpendicular magnetic recording medium product such as a hard disk of a hard disk drive may comprise a functional layer corresponding to a full magnetic stack (e.g., a magnetically soft underlayer, one or more interlayers, and a magnetically hard perpendicular recording layer). In another example, a calibration standard may correspond to a workpiece of the foregoing hard disk in an earlier stage of manufacture. Thus, for example, the calibration standard may comprise a functional layer corresponding to the magnetically soft underlayer, optionally with any intervening layers (e.g., an adhesion layer). In yet another example, it may be determined that a calibration standard corresponding to a perpendicular magnetic recording medium product such as a hard disk of a hard disk drive does not need a functional layer corresponding to a full magnetic stack, as a functional layer comprising a magnetically hard perpendicular recording layer may be sufficient to calibrate an analytical apparatus for workpieces of hard disks having full magnetic stacks. See FIG. 2 and FIG. 4 for an example of a calibration standard 102 comprising a functional layer 222.

With respect to the feature layer, the feature layer may comprise a single layer or a plurality of layers depending upon the analytical apparatus and/or the workpiece (e.g., a workpiece of a product at a particular stage of manufacture) for which the calibration standard is designed. The feature layer of a calibration standard includes, but is not limited to, a single layer or a plurality of layers responsible for imparting pre-determined features to the calibration standard; the feature layer may comprise any material suitable for the lithographic process provided herein below, including, but not limited to silicon and tantalum. The feature layer may be distinct from each of the other layers of a calibration standard, and the feature layer may overlie or underlie some of the other layers of the calibration standard. For example, see calibration standard 102 in FIG. 2 after Step 3a, which calibration standard 102 comprises a distinct feature layer 228 overlying functional layer 222 and underlying finish layer 226. For another example, see calibration standard 102 in FIG. 2 after Step 4c, which calibration standard 102 comprises a distinct feature layer 228 overlying functional layer 222. For yet another example, see calibration standard 102 in FIG. 4 after Step 8, which calibration standard 102 comprises a distinct feature layer 228 underlying each of functional layer 222 and finish layer 226. The feature layer may also be indistinct from one or more of the other layers of a calibration standard. For example, see calibration standard 102 in FIG. 2 after Step 4b, which calibration standard 102 comprises a feature layer 228 comprising functional layer 222.

With respect to the optional finish layer, the finish layer may comprise a single layer or a plurality of layers depending upon the analytical apparatus and/or the workpiece (e.g., a workpiece of a product at a particular stage of manufacture) for which the calibration standard is designed. The finish layer of a calibration standard includes, but is not limited to, a single layer or a plurality of layers corresponding to a workpiece's finish layer(s) at a later stage of manufacture. The finish layer may comprise, for example, a protective overcoat overlying the functional layer or the feature layer. For example, see calibration standard 102 in FIG. 2 after Step 3a, which calibration standard 102 comprises a finish layer 226 overlying feature layer 228. For another example, see calibration standard 102 in FIG. 4 after Step 8, which calibration standard 102 comprises a finish layer 226 overlying functional layer 222. The finish layer may comprise any material suitable for the lithographic process provided herein below, including, but not limited to, carbon, colloid-occluded carbon, diamond-like carbon, silicon, silicon dioxide, metal, or ceramic material. In some embodiments, the finish layer may further comprise, for example, a lubricant such as perfluoropolyether ("PFPE") material overlying the protective layer.

In addition to the foregoing description for the functional layer, feature layer, and optional finish layer, the thickness of each layer may vary. In some embodiments, the thickness of the functional layer, feature layer, and/or optional finish layer may be at least 0.25 nm, 0.5 nm, 1 nm, 2 nm, 3 nm, 4 nm, 5 nm, 10 nm, 25 nm, 50 nm, 75 nm, 100 nm, 125 nm, 150 nm, 175 nm, 200 nm, 225 nm, 250 nm, 275 nm, 300 nm, 400 nm, or 500 nm. In some embodiments, the thickness of the functional layer, feature layer, and/or optional finish layer may be no more than 500 nm, 400 nm, 300 nm, 275 nm, 250 nm, 225 nm, 200 nm, 175 nm, 150 nm, 125 nm, 100 nm, 75 nm, 50 nm, 25 nm, 10 nm, 5 nm, 4 nm, 3 nm, 2 nm, 1 nm, 0.5 nm, or 0.25 nm. Combinations of the foregoing may also be used to describe the thickness of the functional layer, feature layer, and/or optional finish layer. In some embodiments, for example, the thickness of the functional layer, feature layer, and/or optional finish layer may be at least 0.25 nm and no more than 500 nm (i.e., between 0.25 nm and 500 nm), such as at least 1 nm and no more than 200 nm (i.e., between 1 nm and 200 nm), including at least 1 nm and no more than 100 nm (i.e., between 1 nm and 100 nm).

With respect to pre-determined features, the pre-determined features of a calibration standard comprise a plurality of features designed into the calibration disk that correspond to potential defects in a workpiece up to a particular stage of manufacture. Such pre-determined features may be incorporated into a calibration disk by application of one or more feature layers during the lithographic process provided herein.

The pre-determined features may be of any structure and/or composition, as long as the structure and/or composition of the pre-determined features is known. The pre-determined features of a calibration standard may comprise a single or multi-layered structure having a composition in accordance with any of a functional layer, a feature layer, a finish layer, or a combination of the foregoing layers. In some embodiments, the pre-determined features may comprise a single or multi-layered structure having a composition in accordance with the functional layer of a calibration standard. For example, see calibration standard 102 in FIG. 2 after Step 4b, which calibration standard 102 comprises pre-determined features in accordance with functional layer 222 (also feature layer 228). In some embodiments, the pre-determined features may comprise a single or multi-layered structure having a composition in accordance with the feature layer of a calibration standard. For example, see calibration standard 102 in FIG. 2 after Step 4c, which calibration standard 102 comprises pre-determined features in accordance with feature layer 228. In some embodiments, the pre-determined features may a single or multi-layered structure having a composition in accordance with a combination of any of a functional layer, a feature layer, or a finish layer. For example, see calibration standard 102 in FIG. 2 after Step 3a, which calibration standard 102 comprises pre-determined features in accordance with a combination of feature layer 228 and finish layer 226. For another example, see calibration standard 102 in FIG. 4 after Step 8, which calibration standard 102 comprises pre-determined features in accordance with a combination of feature layer 228, functional layer 222, and finish layer 226.

The pre-determined features may be in any form, as long as the form of the pre-determined features is known. For example, the pre-determined features may be in pit form or bump form, wherein pits may represent occlusions in a workpiece, and wherein bumps may represent inclusions in a workpiece. The calibration standard may comprise pre-determined features of different forms on the same calibration standard, as long as the different forms are known.

The pre-determined features may be of any dimensions, as long as the dimensions of the pre-determined features are known. The pre-determined features, whether in pit form or bump form, may each vary with respect to height or depth. In some embodiments, the height or depth of a pre-determined feature may be at least 1 nm, 5 nm, 10 nm, 25 nm, 50 nm, 75 nm, 100 nm, 125 nm, 150 nm, 175 nm, 200 nm, 300 nm, 400 nm, 500 nm, or 1000 nm. In some embodiments, the height or depth of a pre-determined feature may be no more than 1000 nm, 500 nm, 400 nm, 300 nm, 200 nm, 175 nm, 150 nm, 125 nm, 100 nm, 75 nm, 50 nm, 25 nm, 10 nm, 5 nm, or 1 nm. Combinations of the foregoing may also be used to describe the height or depth of a pre-determined feature. In some embodiments, for example, the height or depth of a pre-determined feature may be at least 1 nm and no more than 1000 nm (i.e., between 1 nm and 1000 nm), such as at least 50 nm and no more than 200 nm (i.e., between 50 nm and 200 nm), including at least 75 nm and no more than 125 nm (i.e., between 75 nm and 125 nm). The calibration standard may comprise pre-determined features of different heights and depths on the same calibration standard, as long as the heights and depths are known.

Again, the pre-determined features may be of any dimensions, as long as the dimensions of the pre-determined features are known. The pre-determined features, whether in pit form or bump form, may each vary with respect to diameter, length, and width. In some embodiments, the diameter, the length, or the width of a pre-determined feature may be at least 1 nm, 5 nm, 10 nm, 25 nm, 50 nm, 75 nm, 100 nm, 125 nm, 150 nm, 175 nm, 200 nm, 300 nm, 400 nm, 500 nm, or 1000 nm. In some embodiments, the diameter, the length, or the width of a pre-determined feature may be no more than 1000 nm, 500 nm, 400 nm, 300 nm, 200 nm, 175 nm, 150 nm, 125 nm, 100 nm, 75 nm, 50 nm, 25 nm, 10 nm, 5 nm, or 1 nm. Combinations of the foregoing may also be used to describe the diameter, the length, or the width of a pre-determined feature. In some embodiments, for example, the diameter, the length, or the width of a pre-determined feature may be at least 1 nm and no more than 1000 nm (i.e., between 1 nm and 1000 nm), such as at least 50 nm and no more than 200 nm (i.e., between 50 nm and 200 nm), including at least 75 nm and no more than 125 nm (i.e., between 75 nm and 125 nm). The calibration standard may comprise pre-determined features of different diameters, lengths, and widths on the same calibration standard, as long as the diameters, the lengths, and the widths are known.

The pre-determined features may be in any location about the calibration standard, as long as the location of the pre-determined features is known. For example, the location of the pre-determined features may be in accordance with a Cartesian coordinate system, a polar coordinate system, a log-polar coordinate system, an elliptic coordinate system, or the like.

The pre-determined features may be in any arrangement, as long as the arrangement of the pre-determined features is known (i.e., pre-determined). In some embodiments, the pre-determined features may be consistently arranged in accordance with a coordinate system, wherein a pre-determined subset of coordinates in the coordinate system comprises a pre-determined feature. For example, the pre-determined features may be consistently arranged in accordance with a coordinate system, wherein each coordinate, every other coordinate, every third coordinate, etc. of the coordinate system comprises a pre-determined feature. In some embodiments, the pre-determined features may be inconsistently arranged in accordance with a coordinate system, wherein a pre-determined subset of coordinates in the coordinate system comprises a pre-determined feature. For example, the number of pre-determined features per unit area of a certain region (e.g., annulus, quadrant, etc.) of a calibration disk may be greater or less than the number of pre-determined features per unit area of another region (e.g., another annulus, another quadrant, etc.) of a calibration disk.

Further with respect to the arrangement of pre-determined features about the calibration standard, the pitch between pre-determined features (i.e., the translational distance from like pre-determined features) may vary. In some embodiments, the pitch between pre-determined features be at least 1 µm, 5 µm, 10 µm, 25 µm, 50 µm, 75 µm, 100 µm, 125 µm, 150 µm, 175 µm, 200 µm, 300 µm, 400 µm, 500 µm, 1000 µm, 1500 µm, 2000 µm, 2500 µm, 3000 µm, 3500 µm, 4000 µm, 4500 µm, or 5000 µm. In some embodiments, the pitch between pre-determined features may be no more than 5000 µm, 4500 µm, 4000 µm, 3500 µm, 3000 µm, 2500 µm, 2000 µm, 1500 µm, 1000 µm, 500 µm, 400 µm, 300 µm, 200 µm, 175 µm, 150 µm, 125 µm, 100 µm, 75 µm, 50 µm, 25 µm, 10 µm, 5 µm, or 1 µm. Combinations of the foregoing may also be used to describe the pitch between pre-determined features. In some embodiments, for example, the pitch between pre-determined features may be at least 1 µm and no more than 5000 µm (i.e., between 1 µm and 5000 µm), such as at least 1 µm and no more than 1000 µm (i.e., between 1 µm and 1000 µm), including at least 50 µm and no more than 200 µm (i.e., between 50 µm and 200 µm) and at least 75 µm and no more than 125 µm (i.e., between 75 µm and 125 µm).

The pre-determined features may occur in any number, as long as the number of the pre-determined features is known. In some embodiments, the number of pre-determined features may be at least 1, 10, 50, 100, 250, 500, 750, 1000, 1500, 2000, 2500, 3000, 3500, 4000, 4500, 5000, 5500, 6000, 6500, 7000, 7500, 8000, 8500, 9000, 9500, or 10,000. In some embodiments, the number of pre-determined features may be no more than 10,000, 9500, 9000, 8500, 8000, 7500, 7000, 6500, 6000, 5500, 5000, 4500, 4000, 3500, 3000, 2500, 2000, 2500, 2000, 1500, 1000, 750, 500, 250, 100, 50, 10, 1. Combinations of the foregoing may also be used to describe the number of pre-determined features. In some embodiments, for example, the number of pre-determined features may be at least 1 and no more than 10,000 (i.e., between 1 and 10,000), such as at least 1000 and no more than 8,000 (i.e., between 1000 and 8000), including at least 4500 and no more than 6500 (i.e., between 4500 and 6500). The higher the number of pre-determined features on a calibration standard, the higher the accuracy of calibration of the analytical instrument being calibrated with the calibration standard.

Specifications may provide detailed information about the pre-determined features of the calibration standards described herein. Such detailed information may include, but is not limited to, information regarding the structure, composition, form (e.g., pit, bump, etc.), dimensions (e.g., height, depth, diameter, length, width, etc.), and location of each pre-determined feature of a calibration standard. Such detailed information may further include the number of pre-determined features of a calibration standard, as well as and the arrangement of the predetermined features of the calibration standard. Prior to calibration of an analytical apparatus, specifications comprising detailed information about the pre-determined features of a calibration disk may be provided to a database on a computer. Such specifications may be held on a storage medium for digitized information that may conveniently be used to provide the detailed information to the database of the computer. In some embodiments, the storage medium may be an optical disc such as a compact disc ("CD"), a digital versatile disc ("DVD"), or a Blu-ray ("BD") disc; a solid-state device such as a universal serial bus ("USB") flash drive or a memory card (e.g., CompactFlash I/II, Memory Stick, miniSD, microSD, etc.); a networked solid-state device such as networked solid-state drive, or a networked hard disk drive.

Figure 2:
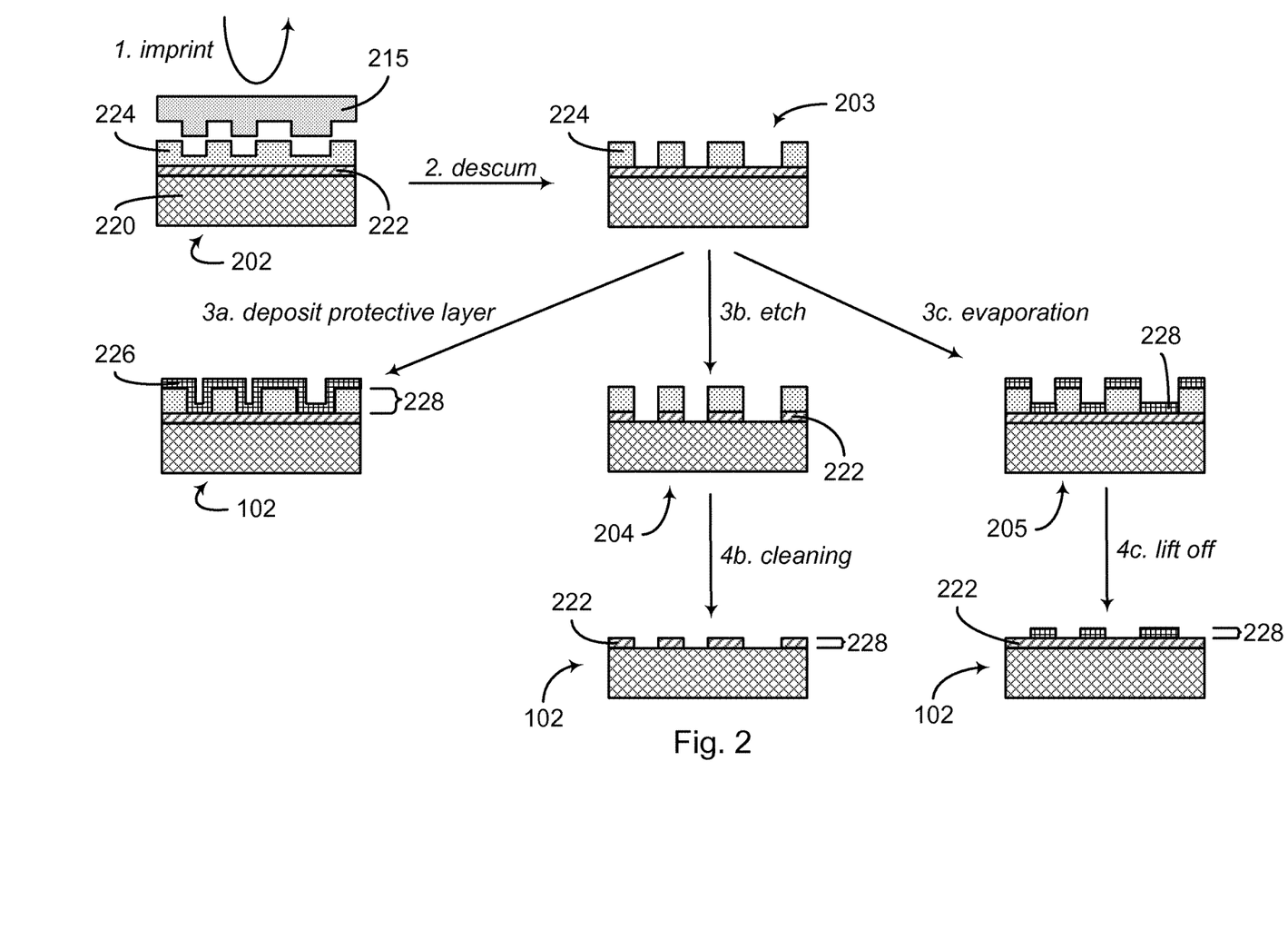
FIG. 2 provides calibration standards and methods for preparing the calibration standards in some embodiments.

Turning to preparation of calibration standards, FIG. 2 provides some different embodiments of calibration standards and some different embodiments by which calibration standards may be lithographically prepared (e.g., using bit-patterned media ["BPM"] technology) beginning with an imprinting step, Step 1. (See Steps 1-3 of FIG. 4 for an embodiment by which calibration standard intermediates may be prepared for imprinting.) In Step 1 of FIG. 2, a resist layer 224 (e.g., a polymer) may be deposited on a calibration standard intermediate 202 comprising a substrate 220, a functional layer 228, and an optional adhesion layer 430 (see FIG. 4), and a template 215 may be used to imprint the resist layer 224. An optional step (not shown) may include curing the resist layer 224 to harden the resist layer after imprinting. In Step 2 of FIG. 2, the calibration standard intermediate 202 may be descummed to remove residual resist (i.e., "scum") left over from imprinting the resist layer 224 and to provide a descummed calibration standard intermediate 203.

Turning to Step 3a of FIG. 2, a finish layer 226 may be deposited on the resist layer 224 of the descummed calibration standard intermediate 203 to provide calibration standard 102 comprising a substrate 220, a functional layer 222, a feature layer 228, and a finish layer 226. An exemplary finish layer 226 that may be deposited on resist layer 224 includes, but is not limited to, carbon, colloid-occluded carbon, diamond-like carbon, silicon, silicon dioxide, metal, or ceramic material.

Turning to Step 3b of FIG. 2, the descummed calibration standard intermediate 203 may be etched to provide an etched calibration standard intermediate 204 comprising a substrate 220, an etched functional layer 222, and a resist layer 224. The etched calibration standard intermediate 204 may be cleaned as in Step 4b of FIG. 4 to provide a calibration standard 102 comprising a substrate 220 and a functional layer 222/feature layer 228.

Turning to Step 3c of FIG. 2, the descummed calibration standard intermediate 203 may be subjected to evaporation-based deposition to provide a calibration standard intermediate 205 comprising a substrate 220, a functional layer 222, a resist layer 224, and a newly deposited layer overlying the functional layer 222 and the resist layer 224. The resist layer 224 and the newly deposited layer thereon may be subjected to a lift-off step as in Step 4c to provide calibration standard 102 comprising a substrate 220, a functional layer 222, and a feature layer 228.

Figure 3A:
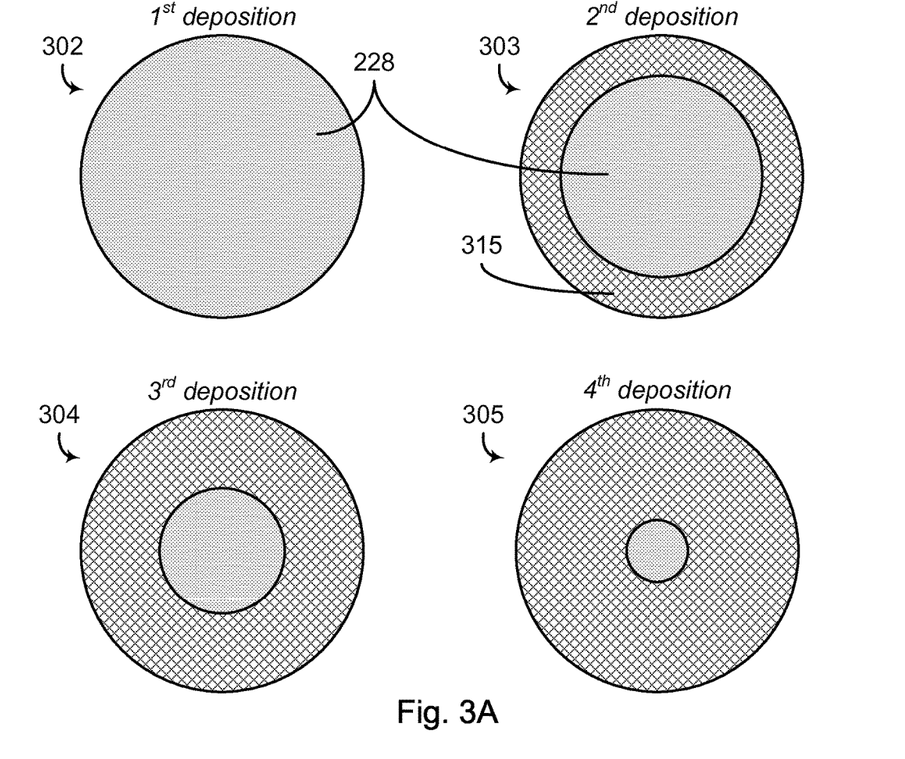
FIG. 3A provides a calibration standard with pre-determined features of different heights and a method for preparing the calibration standard in an embodiment.

FIG. 3A provides a method by which calibration standards (or intermediates thereof) may be lithographically prepared to provide pre-determined features of different heights on individual calibration standards, for example, by annular regions; however, individual calibration standards having pre-determined features of different heights are not limited to the pre-determined features of different heights being in annular regions, as different shaped masks may be used in the following embodiment.

Beginning with an intermediate calibration standard, which may be a naked substrate 202 (e.g., a silicon wafer, a quartz wafer, a glass disk, an aluminum disk, or the like) or a substrate 202 comprising one or more intermediate layers thereon, the intermediate calibration standard may be subjected to a first deposition (e.g., by sputtering, electroplating, atomic layer deposition ["ALD"], chemical vapor deposition ["CVD"], evaporation, ion beam deposition ["IBD"], or the like) to provide an intermediate calibration standard 302 comprising a first deposition layer. The intermediate calibration standard 302 may subsequently be masked with a mask 315 and subjected to a second deposition, which second deposition may be the same or different than the first deposition with respect to material and/or deposition method, to provide an intermediate calibration standard 303 comprising a second deposition layer. The intermediate calibration standard 303 may subsequently be masked with a mask 316 and subjected to a third deposition, which third deposition may be the same or different than the first or second deposition with respect to material and/or deposition method, to provide an intermediate calibration standard 304 comprising a third deposition layer. The intermediate calibration standard 304 may subsequently be masked with a mask 317 and subjected to a fourth deposition, which fourth deposition may be the same or different than the first, second, or third deposition with respect to material and/or deposition method, to provide an intermediate calibration standard 305 comprising a fourth deposition layer.

Figure 3B:
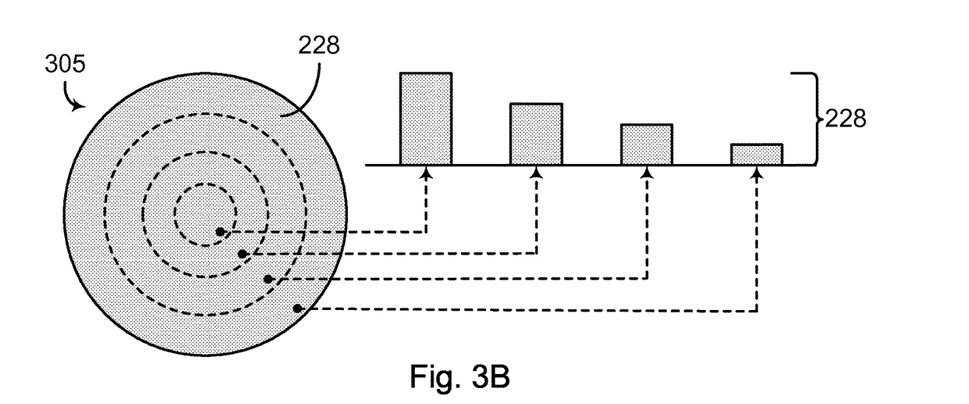
FIG. 3B provides a calibration standard with pre-determined features of different heights in an embodiment.

FIG. 3B provides the intermediate calibration standard 305 of FIG. 3A without mask 317. As shown, the intermediate calibration standard 305 comprises pre-determined features of different heights by annular regions, with the outer annular regions having pre-determined features of a lesser height than the inner annular regions. An intermediate calibration standard such as the intermediate calibration standard 305 is not limited to having pre-determined features of a lesser height at the outer annular regions than at inner annular regions, as different shaped masks may be used as provided herein above. Furthermore, masks of any shape may be applied in any order and in any number to provide the desired pre-determined features. With respect to the number of masks, the number of masks used in a method such as that provided by FIG. 3a may determine the number of different heights for pre-determined features on a calibration standard. For example, two masks provide for pre-determine features of two different heights on a calibration standard; three masks provide for pre-determine features of three different heights on a calibration standard; four masks provide for pre-determine features of four different heights on a calibration standard (as shown); etc. In some embodiments, 2, 3, 4, 5, 6, 7, 8, 9, 10, 11, 12, 13, 14, or 15 masks may be used to provide a respective number of different heights for pre-determined features on a calibration standard.

Figure 4:
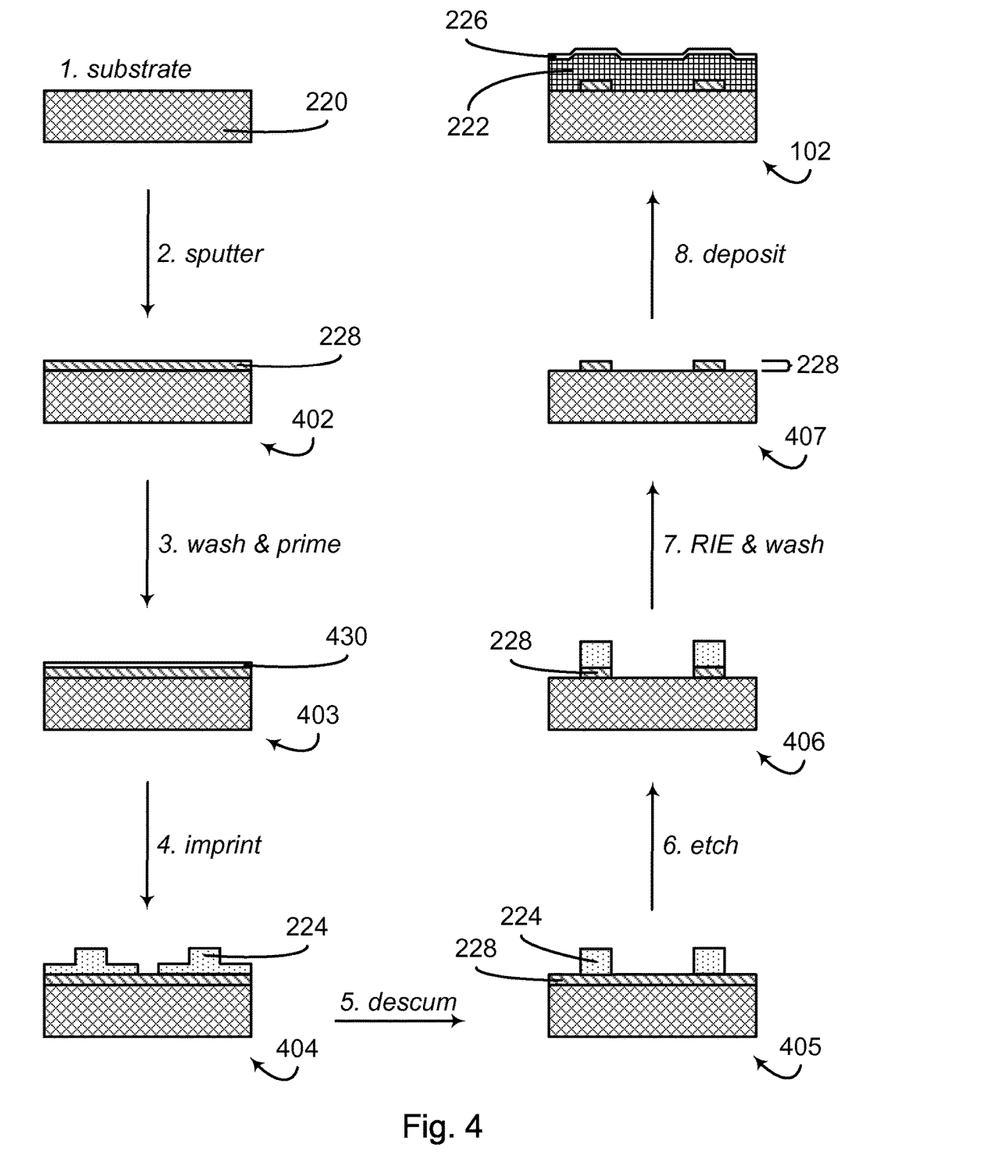
FIG. 4 provides a calibration standard and a method for preparing the calibration standards in an embodiment.

FIG. 4 provides another embodiment of a calibration standard and a different embodiment by which a calibration standard may be lithographically prepared, beginning with a substrate 220. In Step 1 of FIG. 4, a substrate 220 may be provided, which substrate 220 may comprise a silicon wafer, a quartz wafer, a glass disk, an aluminum disk, or the like as described herein above. In Step 2 of FIG. 4, a feature layer 228 may be deposited on the substrate 220 by sputtering; however, Step 2 is not limited to sputtering, as electroplating, atomic layer deposition ("ALD"), chemical vapor deposition ("CVD"), evaporation, ion beam deposition ("IBD"), or the like may also be used. An exemplary feature layer 228 that may be deposited on the substrate 220 includes, but is not limited to chromium. In Step 3 of FIG. 4, the calibration standard intermediate 402 comprising the substrate 220 and feature layer 228 may be washed and primed, which may include the addition of an optional adhesion layer 430 overlying the feature layer 228. In Step 4 of FIG. 4, a resist layer 224 may be deposited on a calibration standard intermediate 403 comprising a substrate 220, a functional layer 228, and an optional adhesion layer 430 (see FIG. 4), and a template 215 may be used to imprint the resist layer 224. In Step 5 of FIG. 4, the calibration standard intermediate 404 may be descummed (e.g., by reactive ion etching ["RIE"] such as $O_2$ RIE) to remove residual resist (i.e., "scum") left over from imprinting the resist layer 224 and to provide a descummed calibration standard intermediate 405. In Step 6 of FIG. 4, the descummed calibration standard intermediate 405 may be etched (e.g., by $Cl_2/O_2$ RIE, which may be used to etch chromium) to provide etched calibration standard intermediate 406 comprising features for which feature layer 228 is named. In Step 7 of FIG. 4, the resist layer 224 may be removed from etched calibration standard intermediate 406, for example, by $O_2$ RIE, and subsequently washed to calibration standard intermediate 407 comprising substrate 220 and feature layer 228. In Step 8 of FIG. 4, calibration standard intermediate 407 may be subjected to a number of deposition steps to provide functional layer 222 and finish layer 226, ultimately providing calibration standard 102 comprising substrate 220, feature layer 228, functional layer 222, and finish layer 226.

As such, provided herein is a lithographic calibration standard, comprising a substrate; a functional layer, wherein the functional layer comprises a composition characteristic of a workpiece of an analytical apparatus; and pre-determined features configured to calibrate the analytical apparatus. In some embodiments, the calibration standard comprises characteristics of a lithographic fabrication process. In some embodiments, the substrate comprises a silicon wafer, a quartz wafer, a glass disk, or an aluminum disk. In some embodiments, the functional layer comprises the pre-determined features. In some embodiments, the functional layer comprises at least one layer, and wherein the at least one layer comprises a composition different than the substrate. In some embodiments, the functional layer comprises a plurality of layers. In some embodiments, the calibration standard further comprises a metal layer directly overlying or underlying the functional layer. In some embodiments, the calibration standard further comprises a resist layer. In some embodiments, the calibration standard further comprises a protective overcoat. In some embodiments, the overcoat comprises carbon, colloid-occluded carbon, diamond-like carbon, silicon, silicon dioxide, a metal, or a ceramic material. In some embodiments, the pre-determined features are arranged in annular regions by height.

Also provided herein is an apparatus, comprising a functional layer overlying a substrate and pre-determined features for calibration of an analytical apparatus configured to measure the surface of a workpiece, wherein the functional layer comprises a composition similar to the workpiece. In some embodiments, the apparatus comprises characteristics of a lithographic fabrication process. In some embodiments, the functional layer comprises at least one layer, and wherein the at least one layer comprises a composition different than the substrate. In some embodiments, the pre-determined features are arranged in annular regions by height.

Also provided herein is a kit, comprising at least one lithographic calibration standard described herein, specifications for the at least one calibration standard, and, optionally, instructions for using the at least one calibration standard with the specifications for the at least one calibration standard. In some embodiments, the specifications are held on a storage medium for digitized information. In some embodiments, the storage medium is an optical disc, a solid-state device, or a networked solid-state device, or a networked hard disk drive.

Also provided herein is an apparatus, comprising a means for providing a lithographic calibration standard comprising a functional layer to the apparatus, wherein the functional layer comprises a composition characteristic of a workpiece of the apparatus; a means for providing calibration standard specifications to a computer interfaced with the apparatus; and a means for calibrating the apparatus in accordance with calibration standard readings and the calibration standard specifications. In some embodiments, the calibration standard further comprises pre-determined features for calibration of the apparatus. In some embodiments, the calibration standard specifications are in accordance with the pre-determined features of the calibration standard. In some embodiments, the means for calibrating the apparatus comprises a means for reading the calibration standard with the apparatus, a means for providing calibration standard readings to the computer, a means for determining differences between the calibration standard readings and the calibration standard specifications, and a means for adjusting the apparatus to minimize differences between the calibration standard readings and the calibration standard specifications. In some embodiments, the means for determining differences between the calibration standard readings and the calibration standard specifications further comprises filtering out calibration standard readings arising from contamination on a surface of the calibration standard. In some embodiments, the apparatus is an optical surface analyzer, magnetic read-write head space analyzer, a scanning probe microscope, an electron microscope, an X-ray scatterometer, or an X-ray diffractometer. In some embodiments, the calibration standard comprises a calibration standard described herein.

Also provided herein is a method, comprising providing a lithographic calibration standard comprising a functional layer to an analytical apparatus, wherein the functional layer comprises a composition characteristic of a workpiece of the analytical apparatus; providing calibration standard specifications to a computer interfaced with the analytical apparatus; and calibrating the analytical apparatus in accordance with calibration standard readings and the calibration standard specifications. In some embodiments, the calibration standard further comprises pre-determined features for calibration of the analytical apparatus. In some embodiments, the calibration standard specifications are in accordance with the pre-determined features of the calibration standard. In some embodiments, calibrating the analytical apparatus comprises reading the calibration standard with the analytical apparatus, providing calibration standard readings to the computer, determining differences between the calibration standard readings and the calibration standard specifications, and adjusting the analytical apparatus to minimize differences between the calibration standard readings and the calibration standard specifications. In some embodiments, determining differences between the calibration standard readings and the calibration standard specifications further comprises filtering out calibration standard readings arising from contamination on a surface of the calibration standard. In some embodiments, the analytical apparatus is an optical surface analyzer, magnetic read-write head space analyzer, a scanning probe microscope, an electron microscope, an X-ray scatterometer, or an X-ray diffractometer. In some embodiments, the calibration standard comprises a calibration standard described herein.

While the invention has been described and/or illustrated by means of various embodiments and/or examples, and while these embodiments and/or examples have been described in considerable detail, it is not the intention of the applicant(s) to restrict or in any way limit the scope of the invention to such detail. Additional adaptations and/or modifications of the invention may readily appear to persons having ordinary skill in the art to which the invention pertains, and, in its broader aspects, the invention may encompass these adaptations and/or modifications. Accordingly, departures may be made from the foregoing embodiments and/or examples without departing from the scope of the invention, which scope is limited only by the following claims when appropriately construed.

What is claimed is:

1. An apparatus, comprising:
    a substrate;
    a functional layer, wherein the functional layer comprises a composition characteristic of a workpiece of an analytical apparatus; and
    a feature layer including pre-determined features configured to calibrate the analytical apparatus.

2. The apparatus of claim 1, wherein the apparatus comprises characteristics of a lithographic fabrication process.

3. The apparatus of claim 1, wherein the functional layer overlies the pre-determined features.

4. The apparatus of claim 1, wherein the functional layer comprises at least one layer, and wherein the at least one layer comprises a composition different than the substrate.

5. The apparatus of claim 1, wherein the functional layer comprises a plurality of layers.

6. The apparatus of claim 1, wherein the apparatus further comprises a metal layer directly overlying the functional layer.

7. The apparatus of claim 1, wherein the apparatus further comprises a resist layer.

8. The apparatus of claim 1, wherein the apparatus further comprises a protective overcoat.

9. The apparatus of claim 8, wherein the protective overcoat comprises carbon, colloid-occluded carbon, diamond-like carbon, a metal, or a ceramic material.

10. The apparatus of claim 1, wherein the pre-determined features are arranged in annular regions by height.

11. An apparatus, comprising:
a functional layer overlying a substrate, wherein the functional layer comprises a composition similar to a workpiece; and
a feature layer including pre-determined features for calibration of an analytical apparatus configured to measure the surface of the workpiece, wherein the pre-determined features of the feature layer correspond to potential defects in the workpiece.

12. The apparatus of claim 11, wherein the functional layer comprises at least one layer, and wherein the at least one layer comprises a composition different than the substrate.

13. The apparatus of claim 11, wherein the pre-determined features are arranged in annular regions by height.

14. A method, comprising:
providing a lithographic calibration standard comprising a functional layer and a feature layer to an analytical apparatus,
wherein the functional layer comprises a composition characteristic of a workpiece of the analytical apparatus;
providing calibration standard specifications to a computer interfaced with the analytical apparatus; and
calibrating the analytical apparatus in accordance with calibration standard readings and the calibration standard specifications.

15. The method of claim 14, wherein the feature layer of the calibration standard comprises pre-determined features for calibration of the apparatus.

16. The method of claim 15, wherein the calibration standard specifications are in accordance with the pre-determined features.

17. The method of claim 14, wherein the means for calibrating the apparatus comprises
reading the calibration standard with the analytical apparatus,
providing calibration standard readings to the computer,
determining differences between the calibration standard readings and the calibration standard specifications, and
adjusting the analytical apparatus to minimize differences between the calibration standard readings and the calibration standard specifications.

18. The method of claim 17, wherein determining differences between the calibration standard readings and the calibration standard specifications further comprises filtering out calibration standard readings arising from contamination on a surface of the calibration standard.

19. The method of claim 14, wherein the analytical apparatus is an optical surface analyzer, magnetic read-write head space analyzer, a scanning probe microscope, an electron microscope, an X-ray scatterometer, or an X-ray diffractometer.

20. The method of claim 14, wherein the calibration standard comprises the apparatus of any one of claims 1-10.

* * * * *